(12) United States Patent
Palackal et al.

(10) Patent No.: US 8,420,563 B2
(45) Date of Patent: Apr. 16, 2013

(54) CATALYST COMPLEX AND PROCESS FOR PRODUCING MULTIMODAL MOLECULAR WEIGHT POLYOLEFINS

(75) Inventors: Syriac Palackal, Munich (DE); Atieh Aburaqabah, Riyadh (SA); Helmut G. Alt, Bayreuth (DE); Christian Goerl, Bayreuth (DE)

(73) Assignee: Saudi Basic Industries Corporation, Riyadh (SA)

( * ) Notice: Subject to any disclaimer, the term of this patent is extended or adjusted under 35 U.S.C. 154(b) by 247 days.

(21) Appl. No.: 12/450,382

(22) PCT Filed: Mar. 5, 2008

(86) PCT No.: PCT/EP2008/001769
§ 371 (c)(1),
(2), (4) Date: Mar. 3, 2010

(87) PCT Pub. No.: WO2008/119431
PCT Pub. Date: Oct. 9, 2008

(65) Prior Publication Data
US 2010/0168351 A1    Jul. 1, 2010

(30) Foreign Application Priority Data

Mar. 29, 2007 (EP) ..................... 07006561

(51) Int. Cl.
*C08F 4/642* (2006.01)
*C08F 4/6592* (2006.01)
*C08F 4/70* (2006.01)
*B01J 31/22* (2006.01)
*C07F 17/00* (2006.01)

(52) U.S. Cl.
USPC ........... 502/113; 502/152; 502/154; 502/155; 526/113; 526/114; 526/160; 526/161; 526/165; 526/169.1; 526/348; 526/352; 526/943; 556/53

(58) Field of Classification Search ............ 502/113, 502/152, 155, 154; 526/113, 114, 160, 161, 526/165, 169.1, 348, 352, 943; 556/53
See application file for complete search history.

(56) References Cited

U.S. PATENT DOCUMENTS 6,544,919 B1 *  4/2003  Tagge et al. .................. 502/113

FOREIGN PATENT DOCUMENTS

| EP | 0964004 A1 | 12/1999 |
| EP | 1777230 A1 | 4/2007 |
| WO | WO 01/25298 A | 4/2001 |
| WO | WO 2005/097837 A1 | 10/2005 |

OTHER PUBLICATIONS

C.K.Gregson, et al. Redox control within Single-Site Polymerization Catalysts;J. Am. Chem Soc Communications. vol. 128, 2006, pp. 7410-7411.

V.C.Gibson, et al. Journal of Organometallic Chem—Elsevier-Sequoia S.A. Lausanne, CH, vol. 690, No. 26, Dec. 15, 2005, pp. 6271-6283.
R.K.J.Bott, et al. Polyhedron, Pergamon Press, Oxford, GB, vol. 25, No. 2, Jan. 23, 2006, pp. 387-396.
A.Shafir, et al. Journal of the Chemical Society, Dalton Trans, Chemical So., Letchworth, GB, No. 4, Jan. 1, 2002, pp. 555-560.
C.Gorl, et al. Journal of Organometallic Chem—Elsevier-Sequoia S.A. Lausanne, CH, vol. 692, No. 26, Nov. 21, 2007, pp. 5727-5753.
European Search Report; European Application No. 07006561.0-2109; Date of Mailing Aug. 31, 2007; 5 pages.
International Search Report; International Application No. PCT/EP2008/001769; International Filing Date Mar. 5, 2008; Date of Mailing Aug. 7, 2008; 3 pages.
Written Opinion of the International Searching Authority; International Application No. PCT/EP2008/001769; International Filing Date Mar. 5, 2008; Date of Mailing Aug. 7, 2008; 6 pages.

* cited by examiner

*Primary Examiner* — Caixia Lu
(74) *Attorney, Agent, or Firm* — Cantor Colburn LLP

(57) ABSTRACT

Multinuclear catalyst complex comprising two or more active metal centers and at least one phenoxyimine derivative and at least one substituted cyclopentadienyl, indenyl or fluorenyl derivative, each phenoxyimine derivative being bonded to a cyclopentadienyl, indenyl or fluorenyl derivative forming a ligand framework, the cyclopentadienyl, indenyl or fluorenyl derivative being coordinated with one of the metal centers and the phenoxyimine derivative being coordinated with an active metal center other than the metal center the cyclopentadienyl, indenyl or fluorenyl derivative is coordinated with, and wherein the phenoxyimine derivative is derived from a phenoxyimine compound of the formula

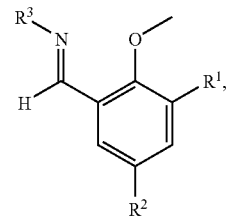

wherein $R^1$ is hydrogen, alkyl, cycloalkyl, aryl or aralkyl;
$R^2$ is hydrogen, halogen, alkyl, cycloalkyl, aryl, O-alkyl or aralkyl; and
$R^3$ is alkyl, cycloalkyl, aryl or aralkyl, process for preparing a multinuclear catalyst composition comprising the steps of bonding the substituted phenoxyimine compound to a substituted cyclopentadienyl, indenyl or fluorenyl derivative to obtain a ligand framework and reacting at least one ligand framework with an active metal component and process for the polymerization of olefins, in particular of ethylene and optionally one or more other a-olefins, wherein said multinuclear catalyst is applied.

15 Claims, No Drawings

CATALYST COMPLEX AND PROCESS FOR PRODUCING MULTIMODAL MOLECULAR WEIGHT POLYOLEFINS

The invention relates to a novel catalyst composition suitable for producing polyolefins having a broad molecular weight distribution (MWD).

Polyolefins having a broad molecular weight distribution (MWD) are attractive for their good processing characteristics. Many ways have been explored to produce such polyolefins. As a first attempt, blends of two or more POs each having a specific molecular weight have been produced. Unless very thoroughly blended, which makes the process expensive, due to the different properties of the blend components segregation of these components easily occurs which makes it difficult to maintain a constant quality of the resulting products. In another approach it has been proposed to apply two or more reactors in series, each having specific conditions and catalysts and each producing a PO having its specific molecular weight. Also these reactor blends tend to segregate.

Also processes have been disclosed where two or more catalysts in one reactor were applied to obtain in one step POs having different molecular weights. Segregation of the two polyolefins having different molecular weights in and after the reactor has appeared to be a serious problem. Another problem in this approach is to find common polymerization conditions where all catalysts show good activity.

Further a combination of a Ziegler-Natta catalyst and a single site catalyst, e.g. a metallocene catalyst, has been proposed. For both types of catalysts hydrogen is commonly used as chain controller for obtaining the desired molecular weight PO. However, usually both types of catalyst require different amounts of hydrogen, making it difficult to obtain the desired molecular weight combination with a reasonable productivity.

In a further approach a Ziegler-Natta catalyst and a single site catalyst have been set on a common support in order to prevent segregation of the different molecular weight components of the multimodal PO. This, however, does not solve the problem of the different hydrogen levels required.

Furthermore it has appeared that any comonomer is built in with preference by the metallocene catalyst, which usually polymerizes the lower molecular weight component. It is desired, however, to have the co-monomer built in into the higher molecular weight fractions of the copolymer to avoid smell and smoke forming during extrusion of the polyolefins.

Aim of the invention is to provide a catalyst that can produce PO compositions having a broad MWD, which do not segregate during transport and other processing.

This aim is achieved, according to the invention by a multinuclear catalyst complex comprising two or more active metal centres and at least one phenoxyimine derivative and at least one substituted cyclopentadienyl, indenyl or fluorenyl derivative, each phenoxyimine derivative being bonded to a cyclopentadienyl, indenyl or fluorenyl derivative forming a ligand framework, the cyclopentadienyl, indenyl or fluorenyl derivative being coordinated with one of the metal centres and the phenoxyimine derivative being coordinated with an active metal centre other than the metal centre the cyclopentadienyl, indenyl or fluorenyl derivative is coordinated with, and wherein the phenoxyimine derivative is derived from a phenoxyimine compound of the formula

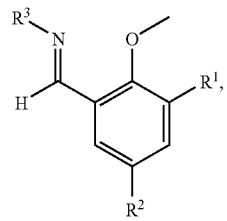

wherein $R^1$ is hydrogen, alkyl, cycloalkyl, aryl or aralkyl;
$R^2$ is hydrogen, halogen, alkyl, cycloalkyl, aryl, O-alkyl or aralkyl; and
$R^3$ is alkyl, cycloalkyl, aryl or aralkyl.

The catalyst complexes according to the invention were found to be applicable for producing polyolefins having broad molecular weight distribution (MWD) showing no segregation in components with different molecular weights. MWD values of at least 15 were found to be easily obtained, values of at least 20, 30 or even more could also be obtained. In olefin copolymers produced with the catalyst complexes according to the invention the comonomers were found to be concentrated almost completely in the higher molecular weight part of the copolymer. The copolymers advantageously did not cause smell and smoke production during processing, in particular during melt extrusion.

A further advantage of the catalyst complex according to the invention is that no hydrogen addition during the polymerization reaction is required to obtain broad MWD polyolefins. If desired hydrogen may be added to further increase the MWD of the polyolefin produced with the catalyst of the invention.

The catalyst complex according to the invention comprises at least one phenoxyimine derivative. Phenoxyimines can coordinate with active metal centres to form catalyst components for olefin, in particular ethylene, polymerization.

The catalyst complex according to the invention comprises at least one substituted cyclopentadienyl, indenyl or fluorenyl derivative. Hereinafter the wording cyclopentadienyl derivative is meant to include also an indenyl or a fluorenyl derivative. Cyclopentadienyl derivatives can coordinate with active metal centres to form catalyst components for olefin polymerization.

Suitable metals to form said catalyst components are all metals known to show catalytic activity in olefin polymerization when coordinated with phenoxyimines or cyclopentadienyl derivatives. Examples of these are Ti, Zr, Hf. Among these Zr is preferred.

Preferably the catalyst complex according to the invention comprises two ligand frameworks, wherein the phenoxyimine derivatives of the two ligand frameworks are coordinated with the same active metal centre and the cyclopentadienyl derivatives of said frameworks are coordinated with separate active metal centres. This complex contains three active sites, one coordinated with the phenoxyimine derivative part of the two ligand frameworks and two coordinated with the cyclopentadienyl derivatives, forming two metallocene catalyst centres. This complex was found to be very active and give broad MWD, e.g. of at least 30.

It was found preferable to keep the differently coordinated active centres separated to avoid mutual negative influence, e.g. to allow the bulky polymer particles to grow without hindering each other.

Substitution of at least one of the phenoxyimine or Cp compounds ligands with an ω-alkynyl group appeared to be a very effective way of separating the metal centres. Substituting the other ligand with a proper substituent, e.g. a halogen, preferably bromo or, more preferably iodo substituent allows bonding the two ligand parts employing palladium catalyzed Sonogashira coupling reactions.

The invention further relates to a process for the synthesis of multinuclear transition metal complexes useful for the polymerization of olefins, in particular ethylene, after activation with appropriate co-catalysts.

In particular this is a process for preparing a multinuclear catalyst complex comprising the steps of bonding at least one substituted phenoxyimine compound to at least one substituted cyclopentadienyl derivative to obtain at least one ligand framework and reacting the at least one ligand framework with an active metal component by deprotonation of the phenoxyimine compounds and of the Cp derivatives and subsequent reaction with a metal salt. The complexes obtained contain differently surrounded metal centres resulting from the combination of the different ligand precursors.

To enable the phenoxyimine and the Cp component to be bonded they should be substituted with mutually reactive substituents. It was found advantageous to substitute at least one of the two components with an omega-alkynyl group and the other one with a halogen, preferably bromo- or iodo substituent, which is reactive with the alkynyl group.

Preferably two ligand frameworks are reacted with the active metal component. The complex obtained in this way was found to be as shown in Schemes 1 and 1a.

Scheme 1

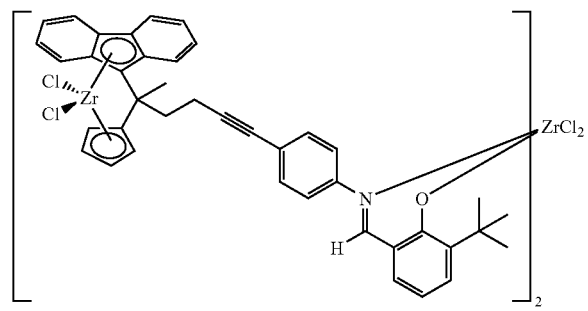

Scheme 1a

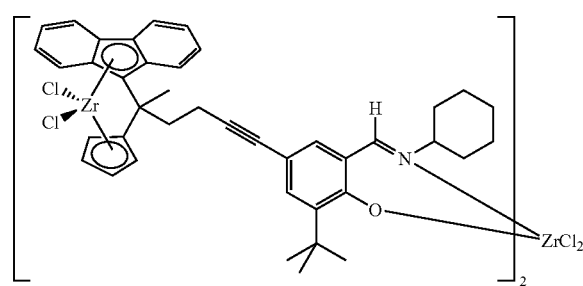

The synthesis of phenoxyimine compounds useful in the complex and process of the invention can be performed starting from substituted phenols, which are reacted with paraformaldehyde yielding salicylaldehyde derivatives according to the reaction scheme shown in Scheme 2. Especially, ortho-monosubstituted phenol derivatives are preferred.

Scheme 2

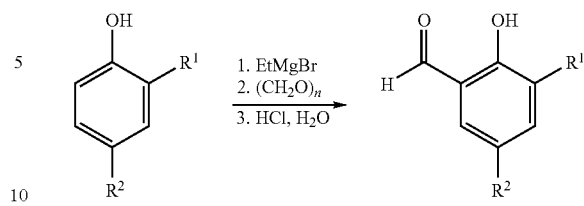

In Scheme 2 $R^1$ can be hydrogen, alkyl, cycloalkyl, aryl and aralkyl; $R^2$ can be hydrogen, halogen, alkyl, cycloalkyl, aryl, O-alkyl and aralkyl.

Introduction of halogen, preferably iodo, substituents into salicylaldehyde derivatives obtained can be accomplished using benzyltrimethylammonium dichloroiodate as the iodinating agent as shown in Scheme 3, where $R^1$ is chosen to be iso-butyl.

Scheme 3

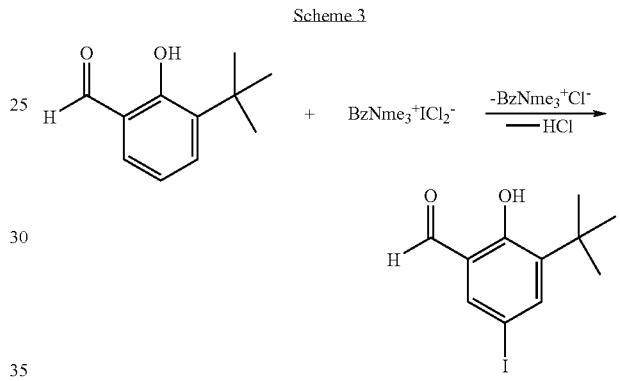

Phenoxyimine compounds can be prepared then by condensation reactions of the substituted salicylaldehydes with aniline or amine derivatives as shown in Scheme 4, where p-TosOH means para-toluene sulphonic acid.

Scheme 4

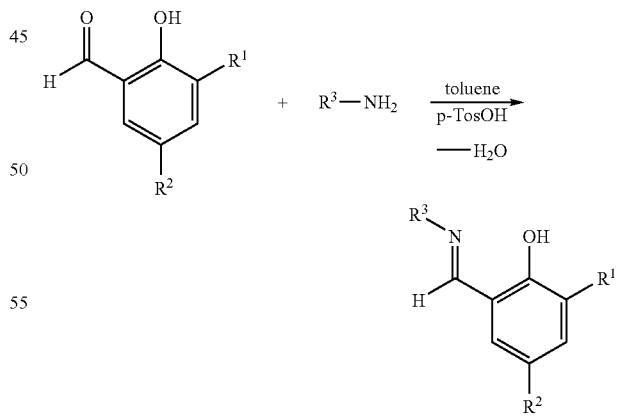

$R^3$ can be alkyl, cycloalkyl, aryl and aralkyl.

Halogen or alkynyl substituted cyclopentadienyl, indenyl, and fluorenyl derivatives can be prepared by direct alkylation of e.g. cyclopentadienylsodium, indenyllithium, or fluorenyllithium (Scheme 5). Furthermore, halogen substituents can be replaced by terminal alkynyl groups in aromatic ring systems (Scheme 5 and 6).

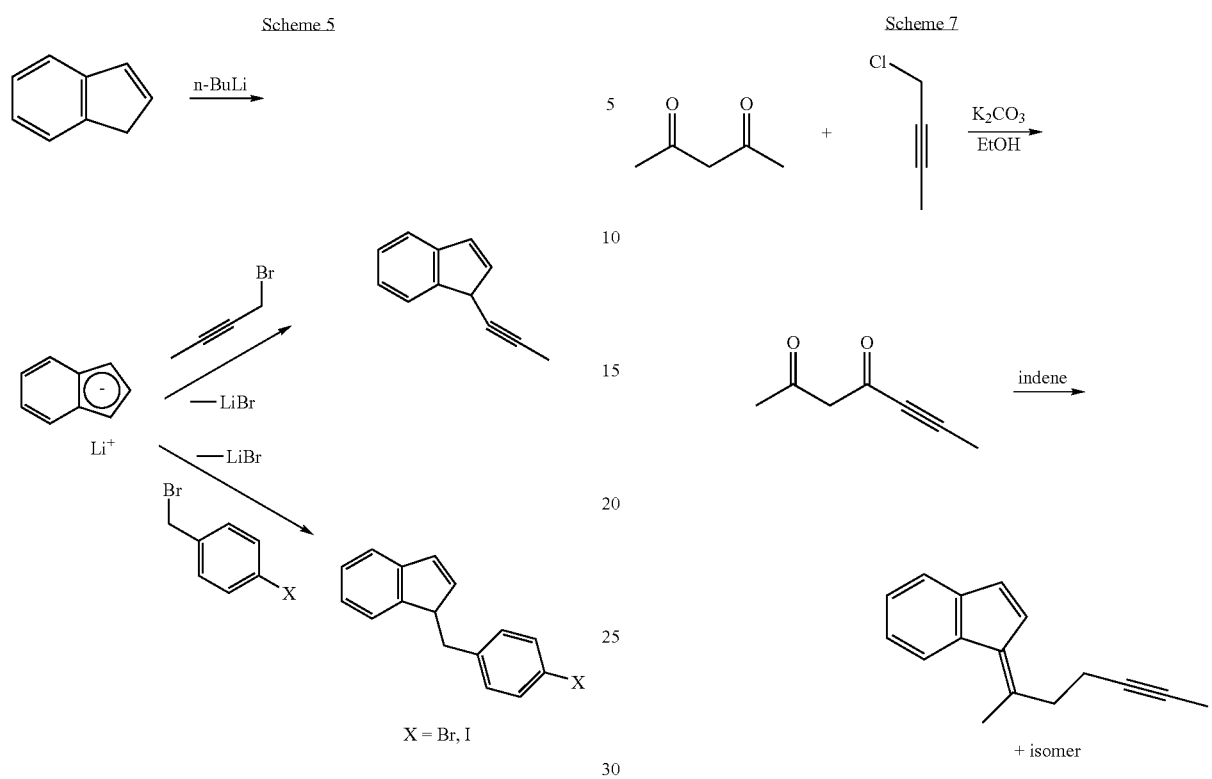

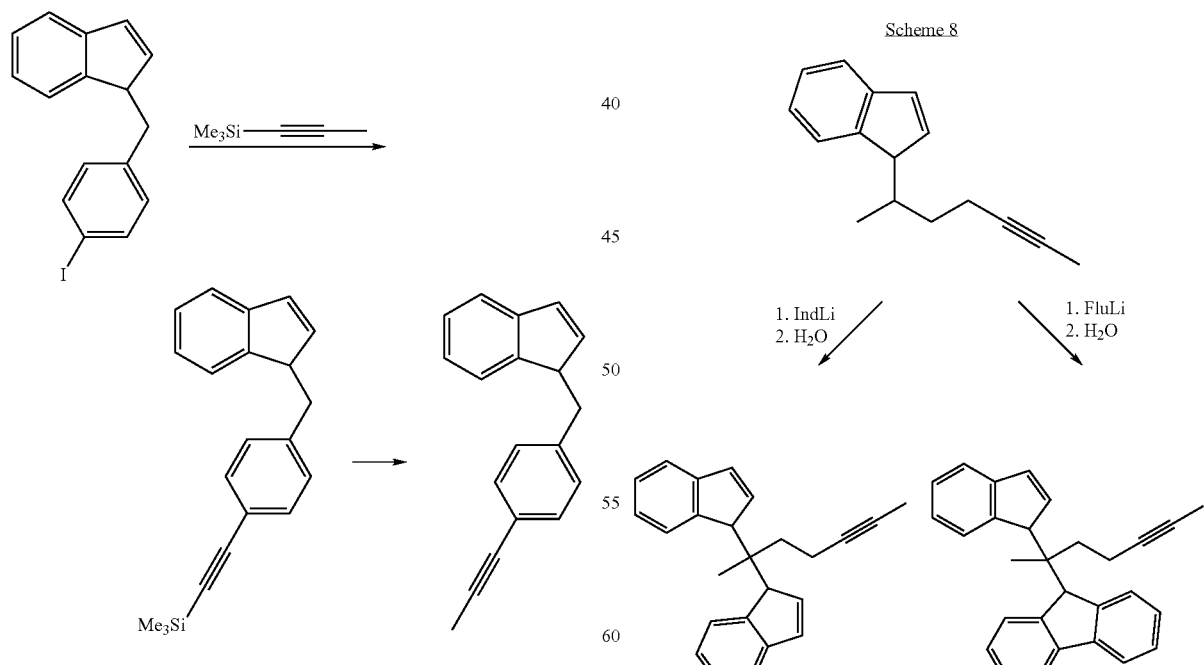

The synthesis of alkynyl substituted bridged metallocene type ligand precursors can be accomplished by the reaction of substituted fulvene derivatives and cyclopentadienylsodium, indenyllithium, or fluorenyllithium (Scheme 7 and 8). As starting materials for the synthesis of fulvenes appropriately substituted ketones can be used.

The bonding of the substituted phenoxyimine compounds and the substituted bridged or unbridged cyclopentadienyl, indenyl, or fluorenyl derivatives is then accomplished by Sonogashira coupling reactions as shown in Scheme 9.

Scheme 9

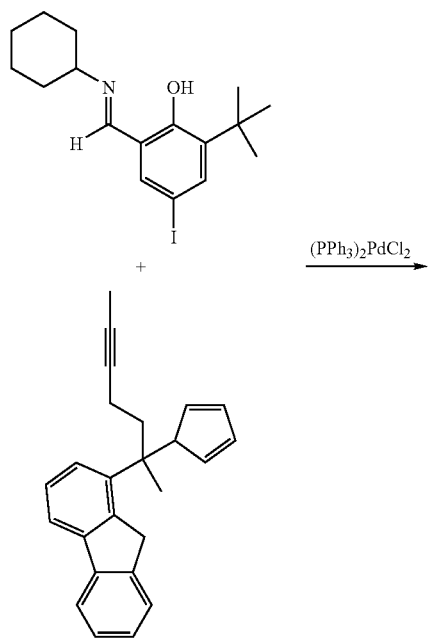

Scheme 10

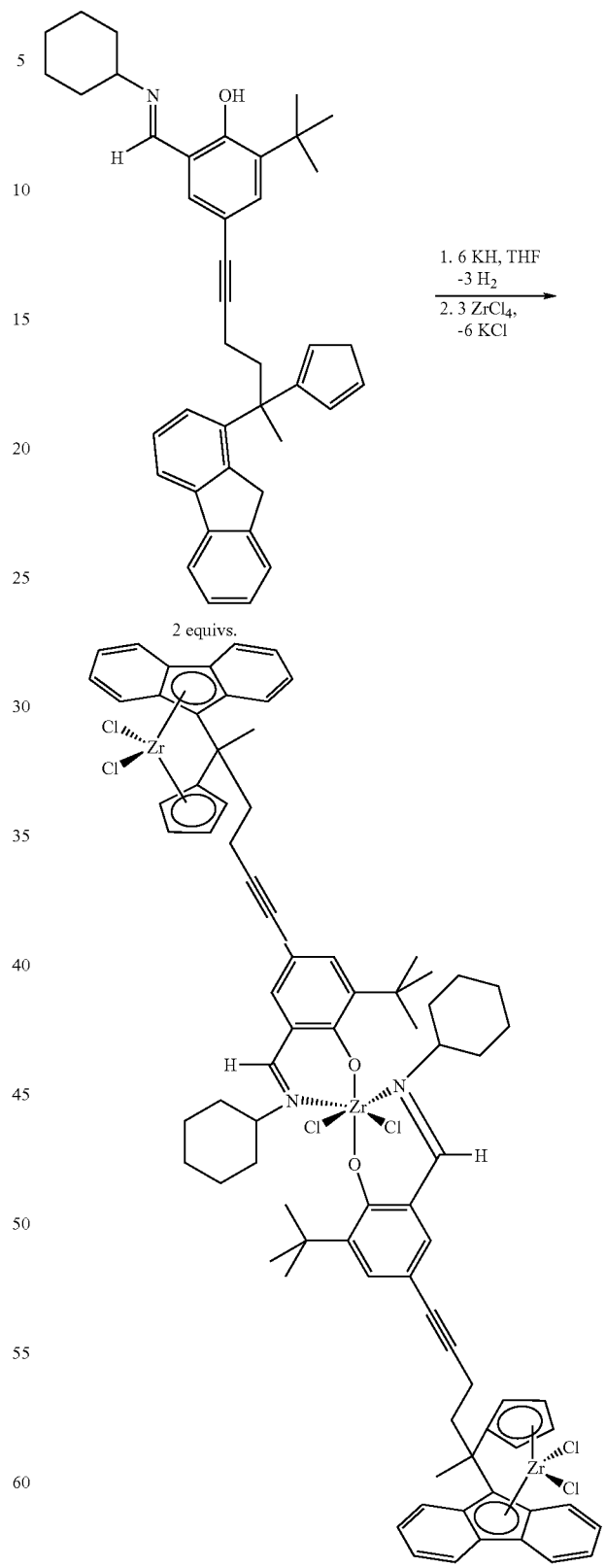

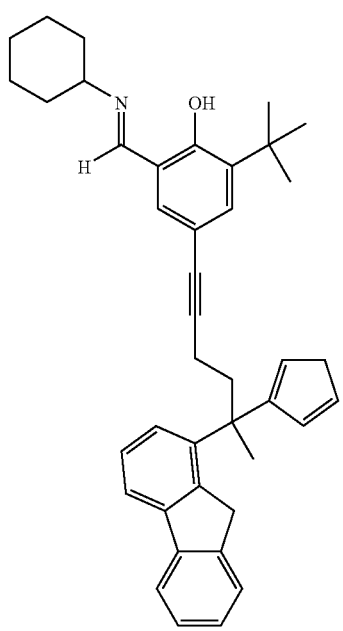

The preparation of the multinuclear catalyst complexes according to the invention from the Sonogashira coupling products of Scheme 9 is performed by deprotonation of the ligand precursors and subsequent reaction with a metal salt. An example of such reaction is shown in Scheme 10, where Zr is used as the metal centres. Other metals can be used to prepare analogue complexes.

A number of catalyst complexes according to the invention were prepared and used as catalyst components for the homogeneous polymerization and oligomerization of ethylene.

The complexes were activated with methylalumoxane (MAO). Other aluminium or boron compounds can also be used as cocatalysts. The polymerization runs were routinely performed at temperatures between 0° C. and +100° C., preferably between 35° C. and 60° C. The employed ethylene pressure is preferably chosen between 0.1 bar and 10 bar. As solvents alkanes or aromatic compounds like toluene can be used.

The multinuclear complexes produce polyethylenes with bimodal, multimodal, or very broad molecular weight distributions resulting from different active centres in the catalyst molecule. The central phenoxyimine moiety produces low or high molecular weight polyethylenes depending on the substitution pattern. In this respect it was found that cycloalkyl substituted phenoxyimines lead to lower molecular weight polymer produced by the phenoxyimine part of the catalyst complex than phenyl and aniline substituted phenoxyimines. Increasing molecular weight was found to be obtained with substituents in the order cyclopropyl<cyclobutyl<cyclopentyl<cyclohexyl<phenyl<aniline.

Since it is also possible to introduce substituents into the aromatic rings of the metallocene moieties, which have a great influence on the molecular weight of the resulting polyethylenes, a wide range of polyethylenes with variable properties is obtainable with the multinuclear, preferably trinuclear catalyst complexes according to the invention.

Further the invention relates to a process for the polymerization of olefins, wherein a catalyst according to any of claim 1 to 5 is applied.

This process surprisingly was found to produce polyolefins having a broad MWD of at least 15 and even more than 20 or even 30.

The catalyst complex according to the invention can be applied unsupported but it can also be applied on the usual support materials, e.g. silica, alumina. It can be applied in the known gas-phase, slurry and solution processes for olefin polymerization.

The process is suitable for producing polyolefin homopolymers of e.g. ethylene and propylene, but also for producing co-polymers of ethylene with one or more higher α-olefins with 3 to 10 C-atoms. Preferably propylene, butene or hexene is used as a comonomer next to ethylene. The amount of comonomer used may depend on the production process, the desired product properties, catalyst used and specific comonomer. These considerations are well known in the art and a skilled person can easily select the proper comonomer and the required amount to obtain the desired product. In general the amount of comonomer used may range from 5-15 wt % for HDPE production and for LLDPE production it may even range from 25 to 50 wt %, based on the total of olefin monomers.

The invention will be elucidated by the following examples, without being restricted thereto.

EXAMPLE 1

Synthesis of 3-tert-butyl salicylaldehyde (1)

To 50 mmol of 2-tert-butyl phenol in 40 ml of tetrahydrofuran was added dropwise a 3-molar methylmagnesium bromide solution (18.5 ml; 55.5 mmol) in diethyl ether. After two hours of stirring at room temperature, gas evolution ceased. About 90% of the solvent were removed in vacuo and toluene (100 ml), triethylamine (10 ml), and paraformaldehyde (3.75 g; 125 mmol) were added. The mixture was heated to 88° C. and held at this temperature for two hours. After cooling down to room temperature, the yellow solution was introduced into cold hydrochloric acid (1M, 250 ml). The organic phase was separated and dried over sodium sulphate. After removal of the solvent in vacuo, 3-tert-butyl salicylaldehyde was purified by high vacuum distillation. Yield: 88%.

EXAMPLE 2

Synthesis of 3-phenyl salicylaldehyde (2)

To 100.6 mmol of 2-phenyl phenol in 40 ml of tetrahydrofuran was added dropwise a 3-molar methylmagnesium bromide solution (36.7 ml; 110 mmol) in diethyl ether. After two hours of stirring at room temperature, gas evolution ceased. About 90% of the solvent were removed in vacuo and toluene (250 ml), triethylamine (20 ml), and paraformaldehyde (7.55 g; 251 mmol) were added. The mixture was heated to 88° C. and held at this temperature for two hours. After cooling down to room temperature, the yellow solution was introduced into cold hydrochloric acid (1M, 250 ml). The organic phase was separated and dried over sodium sulphate. After removal of the solvent in vacuo, 3-phenyl salicylaldehyde was recrystallized from ethanol at −20° C. Yield: 71%.

EXAMPLE 3

Synthesis of 5-chloro-3-cyclohexyl salicylaldehyde (3)

To 100.4 mmol of 4-chloro-2-cyclohexyl phenol in 40 ml of tetrahydrofuran was added dropwise a 3-molar methylmagnesium bromide solution (36.8 ml; 110.4 mmol) in diethyl ether. After two hours of stirring at room temperature, gas evolution ceased. About 90% of the solvent were removed in vacuo and toluene (250 ml), triethylamine (20 ml), and paraformaldehyde (7.53 g; 251 mmol) were added. The mixture was heated to 88° C. and held at this temperature for two hours. After cooling down to room temperature, the yellow solution was introduced into cold hydrochloric acid (1M, 250 ml). The organic phase was separated and dried over sodium sulphate. After removal of the solvent in vacuo, 5-chloro-3-cyclohexyl salicylaldehyde was recrystallized from ethanol at −20° C. Yield: 59%.

EXAMPLE 4

Synthesis of 3-tert-butyl-5-iodosalicylaldehyde (4)

3-tert-butyl salicylaldehyde (1) (8.4 mmol) was dissolved in 100 ml of a mixture of methanol and methylene chloride (3:7). Benzyltrimethylammonium dichloroiodate (3.23 g; 9.2 mmol) and water free calcium carbonate (1.1 g; 11 mmol) were added. After two hours, the excess of calcium carbonate was filtered off. After removal of about 80% of the solvent, 20 ml of a sodium hydrogensulfite solution (5%) was added decolourizing the mixture. Extraction with diethyl ether, drying over sodium sulphate and removal of the solvent yielded the aldehyde as raw product. Purification by recrystallization from n-pentane produced 3-tert-butyl-5-iodosalicylaldehyde in a 48% yield as yellow crystals which are slightly light sensitive and should be stored in the dark.

EXAMPLE 5

Synthesis of N-3-tert-butylsalicylidene-4-iodoaniline (5)

An amount of 5.84 mmol of 3-tert-butyl salicylaldehyde (1) (1.04 g/1 ml) was dissolved in 150 ml of toluene. After addition of 4-iodoaniline (1.53 g/7 mmol/1.2 equivs.) and a few crystals of para-toluenesulfonic acid, the reaction mixture was stirred under reflux for three hours applying a Dean-Stark-trap. After cooling down to room temperature, sodium hydrogencarbonate solution (150 ml) was added. The organic phase was separated and filtered over sodium sulphate and silica. Removing the solvent and recrystallization from ethanol at −20° C. gave the title compound in a 96% yield.

EXAMPLE 6

Synthesis of N-3-tert-butylsalicylidene-4-ethynyl aniline (6)

3-tert-butyl salicylaldehyde (1) (0.70 g/3.93 mmol) and 4-ethynyl aniline (0.49 g/4.2 mmol) were dissolved in 100 ml of ethanol. Molecular sieves (3 Å, 15 g) and a few drops of glacial acetic acid were added and the mixture was stirred at room temperature for three days. After filtration over sodium sulphate and removal of the solvent, the residue was extracted several times with n-pentane. The solution was filtered again over sodium sulphate, and the solvent was removed. The title compound was obtained as a yellow powder. Yield: 43%.

By the same reaction, using toluene as an alternative solvent, other salicylidene derivatives can be synthesised, e.g. N-3-tert-butylsalicylidene propynylamine from 3-tert-butyl salicylaldehyde and propynylamine; N-3-phenylsalicylidene propynylamine from 3-Phenyl salicylaldehyde and propynylamine; and N-5-chloro-3-cyclohexylsalicylidene propynylamine from 5-Chloro-3-cyclohexyl salicylaldehyde and propynylamine.

EXAMPLE 7

Synthesis of N-3-tert-butyl-5-iodosalicylidene cyclopentylamine (7)

An amount of 5.69 mmol of 3-tert-butyl-5-iodo salicylaldehyde (4) (3.71 g) was dissolved in 150 ml of toluene. After addition of cyclopentylamine (0.58 g/6.83 mmol/1.2 equivs.) and a few crystals of para-toluenesulfonic acid, the reaction mixture was stirred under reflux for three hours applying a Dean-Stark-trap. After cooling down to room temperature, sodium hydrogencarbonate solution (150 ml) was added. The organic phase was separated and filtered over sodium sulphate and silica. Removing the solvent resulted in a viscous bright yellow oil that crystallized at room temperature after some days. Yield: 2.10 g (99%)

EXAMPLE 8

Synthesis of N-3-tert-butyl-5-iodosalicylidene cyclohexylamine (8)

An amount of 25.14 mmol of 3-tert-butyl-5-iodo salicylaldehyde (4) (7.64 g) was dissolved in 150 ml of toluene. After addition of cyclohexylamine (2.99 g/30.17 mmol/1.2 equivs.) and a few crystals of para-toluenesulfonic acid, the reaction mixture was stirred under reflux for three hours applying a Dean-Stark-trap. After cooling down to room temperature, sodium hydrogencarbonate solution (150 ml) was added. The organic phase was separated and filtered over sodium sulphate and silica. Removing the solvent resulted in a viscous bright yellow oil that crystallized at room temperature after some days. Yield: 9.76 g (98%).

EXAMPLE 9

Synthesis of N-3-phenylsalicylidene-4-iodoaniline (9)

An amount of 20.6 mmol of 3-phenyl salicylaldehyde (2) (4.08 g) was dissolved in 150 ml of toluene. After addition of 4-iodoaniline (5.42 g/24.8 mmol) and a few crystals of para-toluenesulfonic acid, the reaction mixture was stirred under reflux for three hours applying a Dean-Stark-trap. After cooling down to room temperature, sodium hydrogencarbonate solution (150 ml) was added. The organic phase was separated and filtered over sodium sulfate and silica. Removing the solvent and recrystallization from ethanol at −20° C. gave the title compound as a red solid. Yield: 7.25 g (88%).

EXAMPLE 10

Synthesis of N-5-chloro-3-cyclohexylsalicylidene-4-iodoaniline (10)

An amount of 7.98 mmol of 5-chloro-3-cyclohexyl salicylaldehyde (3) (1.90 g) was dissolved in 150 ml of toluene. After addition of 4-iodoaniline (2.15 g/9.81 mmol) and a few crystals of para-toluenesulfonic acid, the reaction mixture was stirred under reflux for three hours applying a Dean-Stark-trap. After cooling down to room temperature, sodium hydrogencarbonate solution (150 ml) was added. The organic phase was separated and filtered over sodium sulphate and silica. Removing the solvent and recrystallization from ethanol at −20° C. gave the title compound as an orange solid. Yield: 2.95 g (84%).

EXAMPLE 11

Synthesis of 5-hexyn-2-one (11)

2,4-Pentanedione (100 g, 103 ml, 1 mol), anhydrous potassium carbonate (152 g, 1.1 mol), and propargylchloride (71 g, 69 ml, 0.95 mol) were dissolved in 500 ml of ethanol. The reaction mixture was stirred under reflux for 24 hours. After cooling down to room temperature, 300 ml of water were added. The mixture was then extracted with diethyl ether, and the organic phase was washed with brine and dried over sodium sulphate. Removal of the solvent and subsequent vacuum distillation yielded 5-hexyn-2-one as colourless liquid in a 48% yield.

EXAMPLE 12

Synthesis of Fulvene Derivative 12

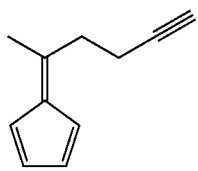

12

Cyclopentadiene (125 mmol) was dissolved in 50 ml of methanol. 5-Hexyn-2-one (50 mmol) and pyrrolidine (75 mmol) were added. The mixture was stirred for 24 hours at 40° C. Glacial acetic acid (100 mmol), water (150 ml) and n-pentane (150 ml) were introduced into the reaction mixture.

The organic phase was separated and dried over sodium sulphate. Vacuum distillation yielded the desired compound as yellow oil (47%).

EXAMPLE 13

Synthesis of Fulvene Derivative 13

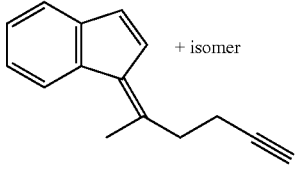
13
+ isomer

Indene (125 mmol) was dissolved in 50 ml of methanol. 5-hexyn-2-one (50 mmol) and pyrrolidine (75 mmol) were added. The mixture was stirred for four days at 40° C. Glacial acetic acid (100 mmol), water (150 ml) and n-pentane (150 ml) were introduced into the reaction mixture. The organic phase was separated and dried over sodium sulphate. Vacuum distillation yielded the desired compound as yellow oil (75%).

EXAMPLE 14

Synthesis of the $C^1$-Bridged Ligand Precursor 14

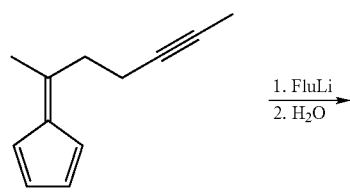
12

1. FluLi
2. H$_2$O

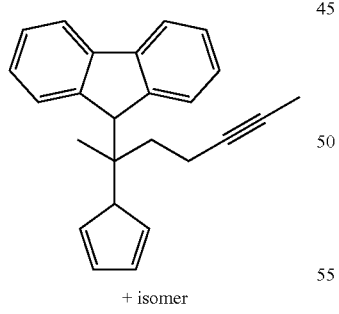
+ isomer
14

Fluorene (30 mmol) was dissolved in 100 ml of diethyl ether and reacted with n-butyllithium (1.6 M, 18.75 ml, 30 mmol). After eight hours, the fulvene derivative 12 (30 mmol) was added, and the mixture was stirred for two hours at room temperature. Hydrolysis was performed adding 50 ml of water. Separation of the organic phase and removal of the solvent yielded a raw product which was recrystallized from n-pentane at −20° C. Yield: 73%.

EXAMPLE 15

Synthesis of the $C^1$-Bridged Ligand Precursor 15

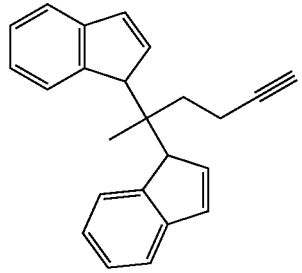
15

Indene (12.4 mmol) was dissolved in 100 ml of diethyl ether and reacted with n-butyllithium (1.6 M, 7.75 ml, 12.4 mmol). After eight hours, the fulvene derivative 13 (12.4 mmol) was added, and the mixture was stirred for two hours at room temperature. Hydrolysis was performed adding 50 ml of water. Separation of the organic phase and removal of the solvent yielded a raw product which was recrystallized from n-pentane at −20° C. Yield: 34%.

EXAMPLE 16

Synthesis of the $C^1$-Bridged Ligand Precursor 16

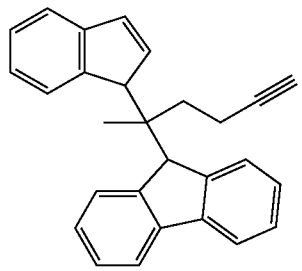
16

Fluorene (35.1 mmol) was dissolved in 100 ml of diethyl ether and reacted with n-butyllithium (1.6 M, 21.95 ml, 35.1 mmol). After eight hours, the fulvene derivative 13 (35.1 mmol) was added, and the mixture was stirred for two hours at room temperature. Hydrolysis was performed adding 50 ml of water. Separation of the organic phase and removal of the solvent yielded a raw product which was recrystallized from n-pentane at −20° C. Yield: 47%.

EXAMPLE 17

Sonogashira Coupling Reaction of Phenoxyimine Compound 8 and the $C^1$-Bridged Ligand Precursor 14

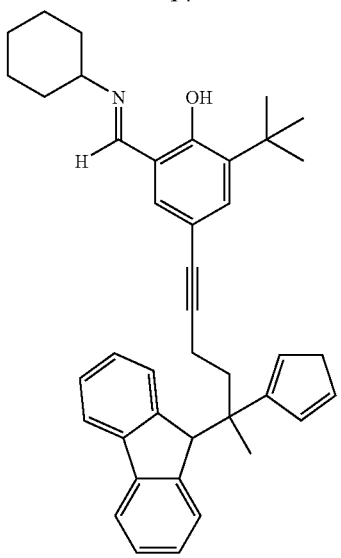
17

In 15 ml of triethylamine, an amount of 1.34 mmol of the phenoxyimine compound 8, the ligand precursor 14 (1.35 mmol), bis(triphenylphosphino)palladium dichloride ($1.35*10^{-5}$ mol/1 mol-%) and copper(I) iodide ($2.7*10^{-5}$ mol/2 mol-%) were dissolved. The mixture was stirred for 20 hours at room temperature. After removal of the solvent, water (50 ml) and n-pentane (50 ml) were added. The organic phase was separated, and the aqueous phase was extracted several times with n-pentane. The combined organic phases were dried over sodium sulphate. Removal of the solvent in vacuo, purification by column chromatography, and recrystallization from n-pentane gave the coupling product 17 as a yellow solid (yield: 94%).

EXAMPLE 18

Sonogashira Coupling Reaction of Phenoxyimine Compound 8 and the $C^1$-Bridged Ligand Precursor 16

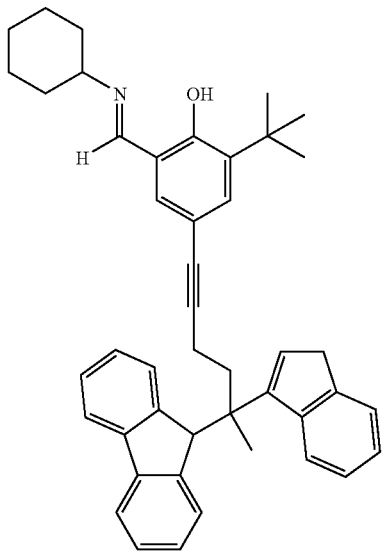

18

In 15 ml of triethylamine, an amount of 1.35 mmol of the phenoxyimine compound 8, the ligand precursor 16 (1.40 mmol), bis(triphenylphosphino)palladium dichloride ($1.4*10^{-5}$ mol/1 mol-%) and copper(I) iodide ($2.8*10^{-5}$ mol/2 mol-%) were dissolved. The mixture was stirred for 20 hours at room temperature. After removal of the solvent, water (50 ml) and n-pentane (50 ml) were added. The organic phase was separated, and the aqueous phase was extracted several times with n-pentane. The combined organic phases were dried over sodium sulphate. Removal of the solvent in vacuo, purification by column chromatography, and recrystallization from n-pentane gave the coupling product 18 as an orange solid (yield: 81%).

EXAMPLE 19

Sonogashira Coupling Reaction of Phenoxyimine Compound 7 and the $C^1$-Bridged Ligand Precursor 14

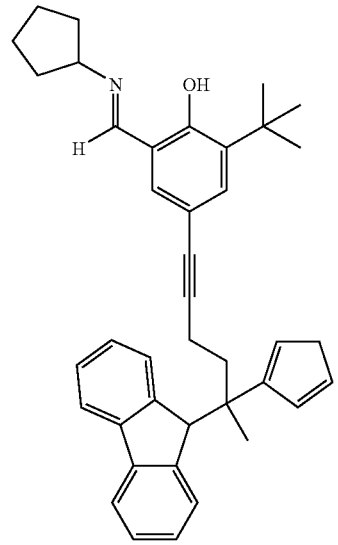

19

In 15 ml of triethylamine, an amount of 1.43 mmol of the phenoxyimine compound 7, the ligand precursor 14 (1.43 mmol), bis(triphenylphosphino)palladium dichloride ($1.43*10^{-5}$ mol/1 mol-%) and copper(I) iodide ($2.86*10^{-5}$ mol/2 mol-%) were dissolved. The mixture was stirred for 20 hours at room temperature. After removal of the solvent, water (50 ml) and n-pentane (50 ml) were added. The organic phase was separated, and the aqueous phase was extracted several times with n-pentane. The combined organic phases were dried over sodium sulphate. Removal of the solvent in vacuo, purification by column chromatography, and recrystallization from n-pentane gave the coupling product 19 as a yellow solid (yield: 86%).

EXAMPLE 20

Sonogashira Coupling Reaction of Phenoxyimine Compound 9 and the $C^1$-Bridged Ligand Precursor 14

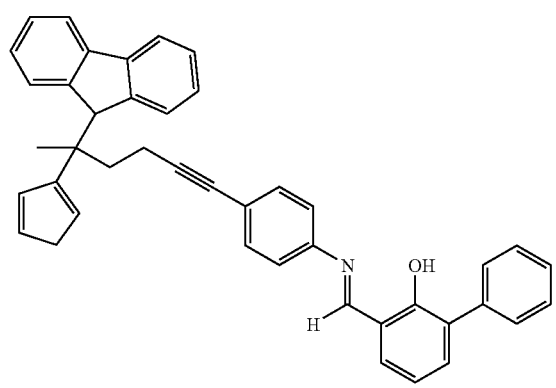

20

In 15 ml of triethylamine, an amount of 1.38 mmol of the phenoxyimine compound 9, the ligand precursor 14 (1.38 mmol), bis(triphenylphosphino)palladium dichloride ($1.38*10^{-5}$ mol/1 mol-%) and copper(I) iodide ($2.76*10^{-5}$ mol/2 mol-%) were dissolved. The mixture was stirred for 20 hours at room temperature. After removal of the solvent, water (50 ml) and n-pentane (50 ml) were added. The organic phase was separated, and the aqueous phase was extracted several times with n-pentane. The combined organic phases were dried over sodium sulphate. Removal of the solvent in vacuo, purification by column chromatography, and recrystallization from n-pentane gave the coupling product 20 as a yellow solid (yield: 68%).

EXAMPLE 21

Sonogashira Coupling Reaction of Phenoxyimine Compound 10 and the $C^1$-Bridged Ligand Precursor 14

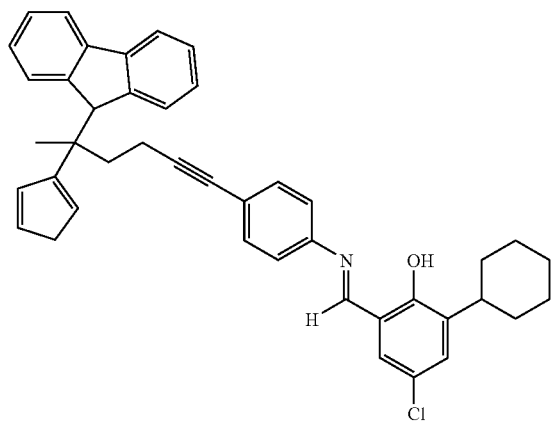

21

In 15 ml of triethylamine, an amount of 1.32 mmol of the phenoxyimine compound 10, the ligand precursor 14 (1.35 mmol), bis(triphenylphosphino)palladium dichloride ($1.35*10^{-5}$ mol/1 mol-%) and copper(I) iodide ($2.7*10^{-5}$ mol/2 mol-%) were dissolved. The mixture was stirred for 20 hours at room temperature. After removal of the solvent, water (50 ml) and n-pentane (50 ml) were added. The organic phase was separated, and the aqueous phase was extracted several times with n-pentane. The combined organic phases were dried over sodium sulphate. Removal of the solvent in vacuo, purification by column chromatography, and recrystallization from n-pentane gave the coupling product 21 as an orange solid (yield: 95%).

EXAMPLE 22

Sonogashira Coupling Reaction of Phenoxyimine Compound 5 and the $C^1$-Bridged Ligand Precursor 14

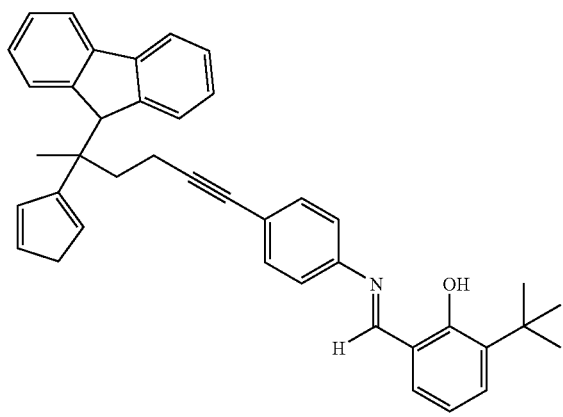

22

In 15 ml of triethylamine, an amount of 1.50 mmol of the phenoxyimine compound 5, the ligand precursor 14 (1.51 mmol), bis(triphenylphosphino)palladium dichloride ($1.51*10^{-5}$ mol/1 mol-%) and copper(I) iodide ($3.02*10^{-5}$ mol/2 mol-%) were dissolved. The mixture was stirred for 20 hours at room temperature. After removal of the solvent, water (50 ml) and n-pentane (50 ml) were added. The organic phase was separated, and the aqueous phase was extracted several times with n-pentane. The combined organic phases were dried over sodium sulphate. Removal of the solvent in vacuo, purification by column chromatography, and recrystallization from n-pentane gave the coupling product 22 as a yellow solid (yield: 86%).

EXAMPLE 23

Sonogashira Coupling Reaction of Phenoxyimine Compound 5 and the $C^1$-Bridged Ligand Precursor 15

In 15 ml of triethylamine, an amount of 2.51 mmol of the phenoxyimine compound 5, the ligand precursor 15 (3.0 mmol), bis(triphenylphosphino)palladium dichloride ($2.51*10^{-5}$ mol/1 mol-%) and copper(I) iodide ($5.02*10^{-5}$ mol/2 mol-%) were dissolved.

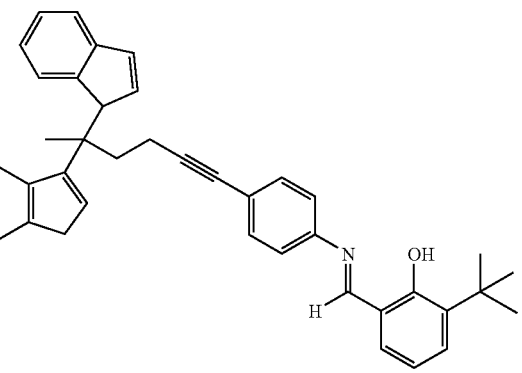

23

The mixture was stirred for 20 hours at room temperature. After removal of the solvent, water (50 ml) and n-pentane (50 ml) were added. The organic phase was separated, and the aqueous phase was extracted several times with n-pentane. The combined organic phases were dried over sodium sulphate. Removal of the solvent in vacuo, purification by column chromatography, and recrystallization from n-pentane gave the coupling product 23 as a slightly brownish solid (yield: 30%).

EXAMPLE 24

Sonogashira Coupling Reaction of Phenoxyimine Compound 5 and the C¹-Bridged Ligand Precursor 16

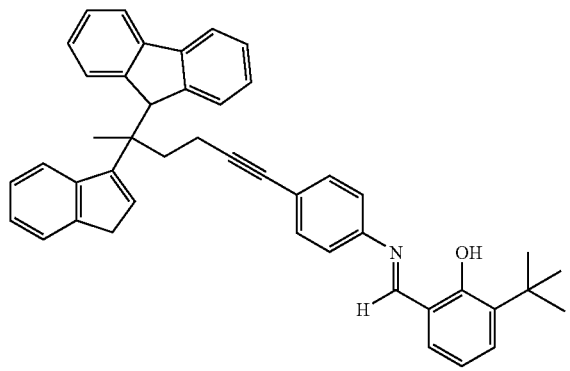

24

In 15 ml of triethylamine, an amount of 3.56 mmol of the phenoxyimine compound 5, the ligand precursor 16 (3.80 mmol), bis(triphenylphosphino)palladium dichloride ($3.56*10^{-5}$ mol/1 mol-%) and copper(I) iodide ($7.12*10^{-5}$ mol/2 mol-%) were dissolved. The mixture was stirred for 20 hours at room temperature. After removal of the solvent, water (50 ml) and n-pentane (50 ml) were added. The organic phase was separated, and the aqueous phase was extracted several times with n-pentane. The combined organic phases were dried over sodium sulphate. Removal of the solvent in vacuo, purification by column chromatography, and recrystallization from n-pentane gave the coupling product 24 as a brownish solid (yield: 38%).

EXAMPLE 25

Synthesis of Trinuclear Complex from Compound 17

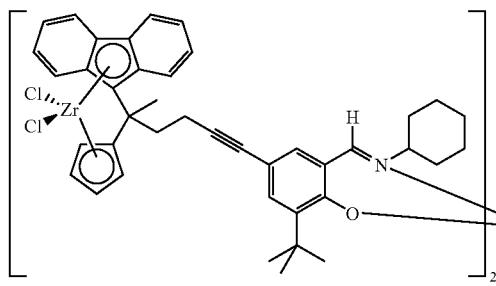

25

An amount of 0.39 mmol of the phenoxyimine compound 17 was dissolved in 30 ml of tetrahydrofuran. Potassium hydride (47 mg/1.18 mmol/3 equivs.), suspended in 10 ml of tetrahydrofuran was added, and the mixture was stirred at room temperature for two hours till the hydrogen evolution had ceased. Zirconium tetrachloride (138 mg/0.59 mmol/1.5 equivs.) was added and stirring was continued for 20 hours. After the solvent was removed in vacuo, methylene chloride (30 ml) was added, and the solution was filtered over sodium sulphate. Removal of about 25 ml of the solvent in vacuo and subsequent addition of 50 ml of n-pentane resulted in the precipitation of a solid. After decanting the overstanding solution, washing with n-pentane (3×15 ml), and drying in vacuo produced complex 25 as an orange powder. Yield: 0.18 g (57%).

EXAMPLE 26

Synthesis of Trinuclear Complex from Compound 18

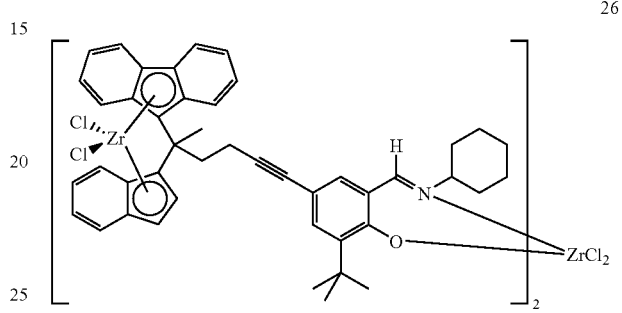

26

An amount of 0.45 mmol of the phenoxyimine compound 18 was dissolved in 30 ml of tetrahydrofuran, then n-butyllithium (0.85 ml/1.36 mmol/3 equivs.) as an 1,6-molar solution in hexanes was added, and the mixture was stirred at room temperature for two hours till the hydrogen evolution had ceased. Zirconium tetrachloride (160 mg/0.69 mmol/1.5 equivs.) was added and stirring was continued for another 20 hours. After the solvent was removed in vacuo, methylene chloride (30 ml) was added, and the solution was filtered over sodium sulphate. Removal of about 25 ml of the solvent in vacuo and subsequent addition of 50 ml of n-pentane resulted in the precipitation of a solid. After decanting the overstanding solution, washing with n-pentane (3×15 ml), and drying in vacuo produced complex 26 as a brownish powder. Yield: 0.21 g (54%).

EXAMPLE 27

Synthesis of Trinuclear Complex from Compound 19

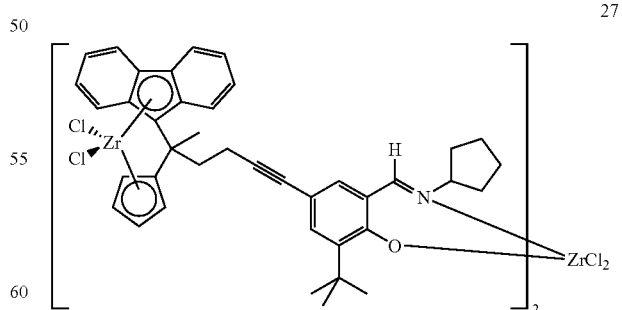

27

An amount of 0.54 mmol of the phenoxyimine compound 19 was dissolved in 30 ml of tetrahydrofuran. Potassium hydride (66 mg/1.63 mmol/3 equivs.), suspended in 10 ml of tetrahydrofuran was added, and the mixture was stirred at room temperature for two hours till the hydrogen evolution had ceased. Zirconium tetrachloride (190 mg/0.82 mmol/1.5 equivs.) was added and stirring was continued for 20 hours. After the solvent was removed in vacuo, methylene chloride (30 ml) was added, and the solution was filtered over sodium sulphate. Removal of about 25 ml of the solvent in vacuo and subsequent addition of 50 ml of n-pentane resulted in the precipitation of a solid. After decanting the overstanding solution, washing with n-pentane (3×15 ml), and drying in vacuo produced complex 27 as a greenish yellow powder. Yield: 0.41 g (95%).

EXAMPLE 28

Synthesis of Trinuclear Complex from Compound 20

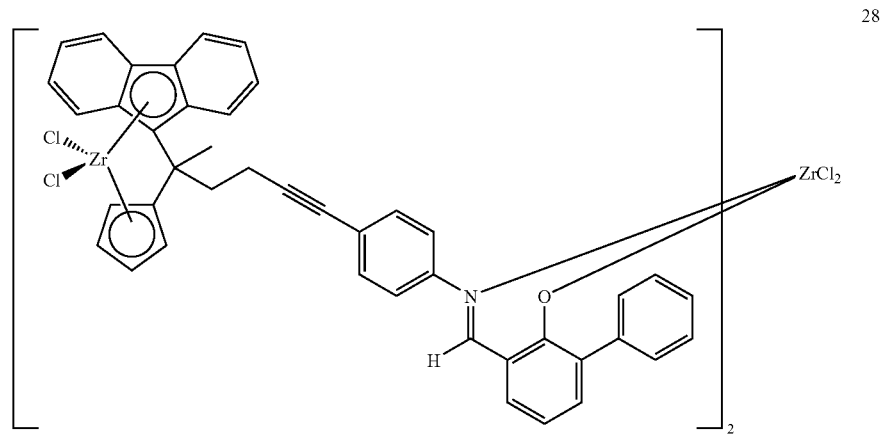

An amount of 0.43 mmol of the phenoxyimine compound 20 was dissolved in 30 ml of tetrahydrofuran. Potassium hydride (52 mg/1.29 mmol/3 equivs.), suspended in 10 ml of tetrahydrofuran was added, and the mixture was stirred at room temperature for two hours till the hydrogen evolution had ceased. Zirconium tetrachloride (150 mg/0.65 mmol/1.5 equivs.) was added and stirring was continued for 20 hours. After the solvent was removed in vacuo, methylene chloride (30 ml) was added, and the solution was filtered over sodium sulphate. Removal of about 25 ml of the solvent in vacuo and subsequent addition of 50 ml of n-pentane resulted in the precipitation of a solid. After decanting the overstanding solution, washing with n-pentane (3×15 ml), and drying in vacuo produced complex 28 as a brownish powder. Yield: 0.31 g (88%).

EXAMPLE 29

Synthesis of Trinuclear Complex from Compound 21

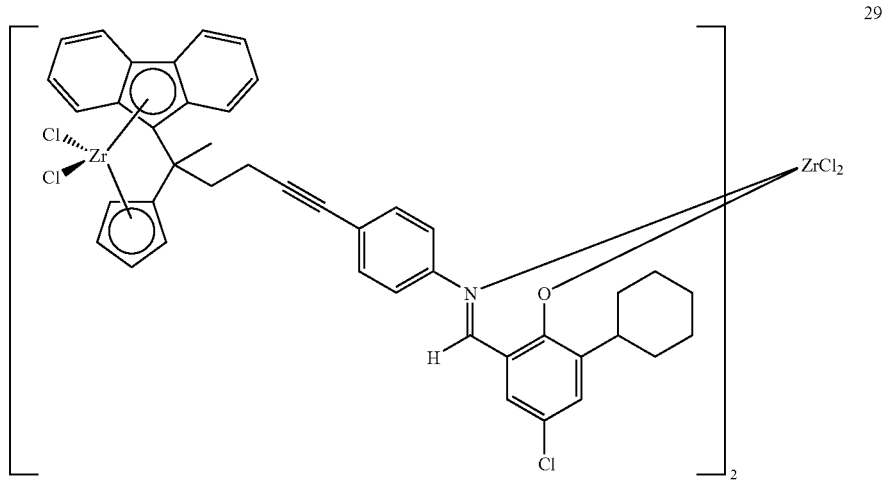

An amount of 0.36 mmol of the phenoxyimine compound 21 was dissolved in 30 ml of tetrahydrofuran. Potassium hydride (43 mg/1.07 mmol/3 equivs.), suspended in 10 ml of tetrahydrofuran was added, and the mixture was stirred at room temperature for two hours till the hydrogen evolution had ceased. Zirconium tetrachloride (124 mg/0.54 mmol/1.5 equivs.) was added and stirring was continued for 20 hours. After the solvent was removed in vacuo, methylene chloride (30 ml) was added, and the solution was filtered over sodium sulphate. Removal of about 25 ml of the solvent in vacuo and subsequent addition of 50 ml of n-pentane resulted in the precipitation of a solid. After decanting the overstanding solution, washing with n-pentane (3×15 ml), and drying in vacuo produced complex 29 as a brownish powder. Yield: 0.30 g (96%).

EXAMPLE 30

Synthesis of Trinuclear Complex from Compound 22

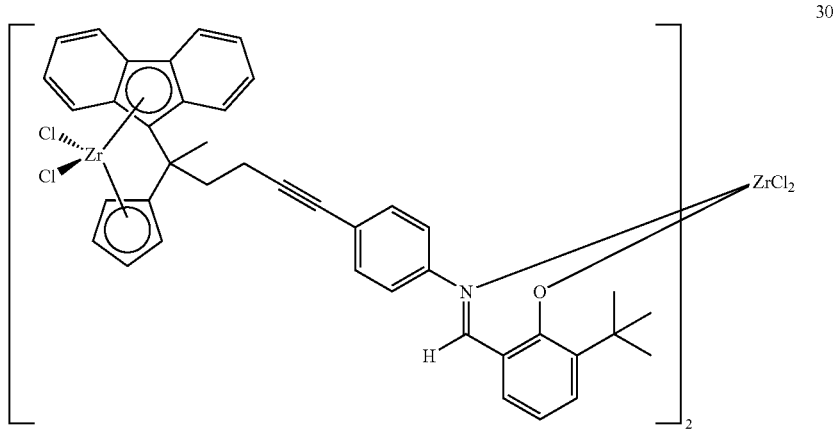

30

An amount of 0.44 mmol of the phenoxyimine compound 22 was dissolved in 30 ml of tetrahydrofuran. Potassium hydride (53 mg/1.32 mmol/3 equivs.), suspended in 10 ml of tetrahydrofuran was added, and the mixture was stirred at room temperature for two hours till the hydrogen evolution had ceased. Zirconium tetrachloride (154 mg/0.66 mmol/1.5 equivs.) was added and stirring was continued for 20 hours. After the solvent was removed in vacuo, methylene chloride (30 ml) was added, and the solution was filtered over sodium sulphate. Removal of about 25 ml of the solvent in vacuo and subsequent addition of 50 ml of n-pentane resulted in the precipitation of a solid. After decanting the overstanding solution, washing with n-pentane (3×15 ml), and drying in vacuo produced complex 30 as a yellow powder. Yield: 0.37 g (95%).

EXAMPLE 31

Synthesis of Trinuclear Complex from Compound 23

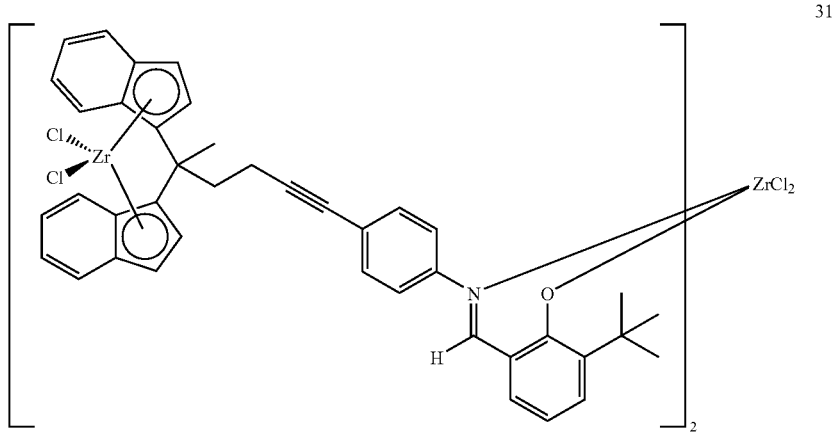

An amount of 0.45 mmol of the phenoxyimine compound 23 was dissolved in 30 ml of tetrahydrofuran. Potassium hydride (54 mg/1.34 mmol/3 equivs.), suspended in 10 ml of tetrahydrofuran was added, and the mixture was stirred at room temperature for two hours till the hydrogen evolution had ceased. Zirconium tetrachloride (157 mg/0.68 mmol/1.5 equivs.) was added and stirring was continued for 20 hours. After the solvent was removed in vacuo, methylene chloride (30 ml) was added, and the solution was filtered over sodium sulphate. Removal of about 25 ml of the solvent in vacuo and subsequent addition of 50 ml of n-pentane resulted in the precipitation of a solid. After decanting the overstanding solution, washing with n-pentane (3×15 ml), and drying in vacuo produced complex 31 as a brownish powder. Yield: 0.14 g (39%).

EXAMPLE 32

Synthesis of Trinuclear Complex from Compound 24

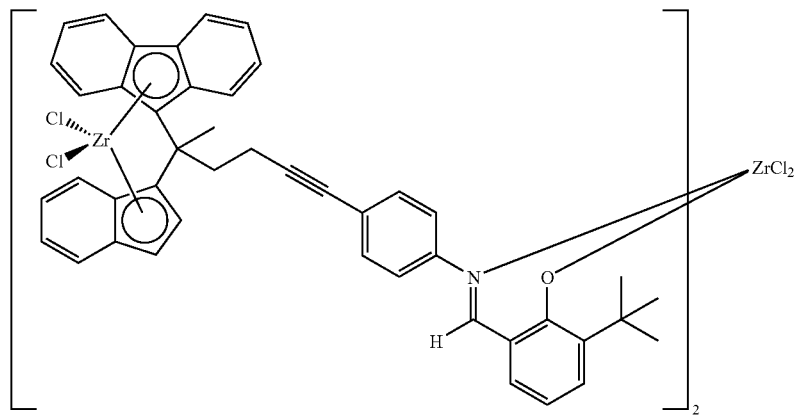

An amount of 0.38 mmol of the phenoxyimine compound 24 was dissolved in 30 ml of tetrahydrofuran. Potassium hydride (48 mg/1.20 mmol/3 equivs.), suspended in 10 ml of tetrahydrofuran was added, and the mixture was stirred at room temperature for two hours till the hydrogen evolution had ceased. Zirconium tetrachloride (133 mg/0.57 mmol/1.5 equivs.) was added and stirring was continued for 20 hours. After the solvent was removed in vacuo, methylene chloride (30 ml) was added, and the solution was filtered over sodium sulphate. Removal of about 25 ml of the solvent in vacuo and subsequent addition of 50 ml of n-pentane resulted in the precipitation of a solid. After decanting the overstanding solution, washing with n-pentane (3×15 ml), and drying in vacuo produced complex 32 as a brownish powder. Yield: 0.11 g (34%).

EXAMPLE 33

General Procedure for the Polymerization of Ethylene in a 1 l Büchi Autoclave

The desired complex (1-10 mg) was suspended in 5 ml of toluene. The mixture was transferred to a 1 l Schlenk flask filled with 250 ml n-pentane. This mixture was transferred to a 1 l Büchi laboratory autoclave under inert atmosphere. An ethylene pressure of 1 bar was applied for five minutes. Methylalumoxane (30% in toluene, Zr:Al=1:500) was added via a cannula, and the autoclave was thermostated to 35° C. applying an ethylene pressure of 10 bar over one hour. The resulting polymer was filtered off over a glass frit, washed with diluted hydrochloric acid, water, and acetone, and finally dried in vacuo.

The properties of the polyethylene obtained with the various catalyst complexes are shown in Table 1.

TABLE 1

Results of ethylene polymerization reactions.

| Catalyst complex | amount of cat. complex [µmol] | amount of polyethylene [g] | activity [kg PE/mol Zr] | $M_n$ [g/mol] | $M_w$ [g/mol] | MWD |
|---|---|---|---|---|---|---|
| 67 | 1.86 | 45.5 | 24500 | 7800 | 134750 | 17.3 |
| 69 | 9.82 | 9.3 | 2840 | 2915 | 125600 | 43.1 |
| 70 | 5.30 | 3.8 | 710 | 6620 | 292900 | 44.3 |
| 71 | 6.55 | 16.9 | 2580 | 10810 | 418500 | 38.7 |

TABLE 1-continued

Results of ethylene polymerization reactions.

| Catalyst complex | amount of cat. complex [µmol] | amount of polyethylene [g] | activity [kg PE/mol Zr] | $M_n$ [g/mol] | $M_w$ [g/mol] | MWD |
|---|---|---|---|---|---|---|
| 72 | 9.68 | 75.2 | 7770 | 7270 | 255400 | 35.1 |
| 73 | 8.97 | 9.5 | 1060 | 5000 | 173500 | 34.6 |
| 74 | 1.95 | 11.0 | 5630 | 9640 | 702550 | 72.9 |

The invention claimed is:

1. A multinuclear catalyst complex comprising two or more active metal centres and at least one phenoxyimine derivative and at least one substituted cyclopentadienyl, indenyl or fluorenyl derivative, each phenoxyimine derivative being bonded to a cyclopentadienyl, indenyl or fluorenyl derivative forming a ligand framework, the cyclopentadienyl, indenyl or fluorenyl derivative being coordinated with one of the metal centres and the phenoxyimine derivative being coordinated with an active metal centre other than the metal centre the cyclopentadienyl, indenyl or fluorenyl derivative is coordinated with, and wherein the phenoxyimine derivative is derived from a phenoxyimine compound of the formula

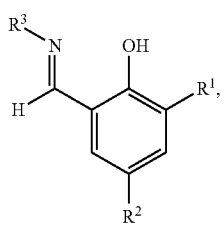

wherein $R^1$ is hydrogen, alkyl, cycloalkyl, aryl or aralkyl;
$R^2$ is hydrogen, halogen, alkyl, cycloalkyl, aryl, O-alkyl or aralkyl; and
$R^3$ is alkyl, cycloalkyl, aryl or aralkyl; and
wherein the phenoxyimine compound and the cyclopentadienyl, indenyl or fluorenyl derivative are bonded by a Sonogashira reaction.

2. A catalyst complex according to claim 1 wherein the metals are chosen from the group consisting of Ti, Hf and Zr.

3. A process for preparing a multinuclear catalyst complex according to claim 1, comprising the steps of bonding a substituted phenoxyimine compound to a substituted cyclopentadienyl, indenyl or fluorenyl derivative to obtain a ligand framework and reacting at least one ligand framework with an active metal component.

4. A process according to claim 3, wherein the metal is selected from the group consisting of Ti, HF and Zr.

5. A process for the polymerization of olefins comprising contacting the olefin with a multinuclear catalyst complex comprising two or more active metal centres and at least one phenoxyimine derivative and at least one substituted cyclopentadienyl, indenyl or fluorenyl derivative, each phenoxyimine derivative being bonded to a cyclopentadienyl, indenyl or fluorenyl derivative forming a ligand framework, the cyclopentadienyl, indenyl or fluorenyl derivative being coordinated with one of the metal centres and the phenoxyimine derivative being coordinated with an active metal centre other than the metal centre the cyclopentadienyl, indenyl or fluorenyl derivative is coordinated with, and wherein the phenoxyimine derivative is derived from a phenoxyimine compound of the formula

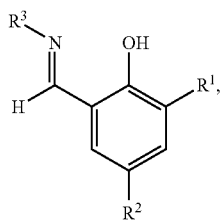

wherein $R^1$ is hydrogen, alkyl, cycloalkyl, aryl or aralkyl;
$R^2$ is hydrogen, halogen, alkyl, cycloalkyl, aryl, O-alkyl or aralkyl; and
$R^3$ is alkyl, cycloalkyl, aryl or aralkyl; and
wherein the phenoxyimine compound and the cyclopentadienyl, indenyl or fluorenyl derivative are bonded by a Sonogashira reaction.

6. The process for polymerization of olefins according to claim 5 wherein the olefin is ethylene.

7. A multinuclear catalyst complex comprising two or more active metal centres and at least one phenoxyimine derivative and at least one substituted cyclopentadienyl, indenyl or fluorenyl derivative, each phenoxyimine derivative being bonded to a cyclopentadienyl, indenyl or fluorenyl derivative forming a ligand framework, the cyclopentadienyl, indenyl or fluorenyl derivative being coordinated with one of the metal centres and the phenoxyimine derivative being coordinated with an active metal centre other than the metal centre the cyclopentadienyl, indenyl or fluorenyl derivative is coordinated with, and wherein the phenoxyimine derivative is derived from a phenoxyimine compound of the formula

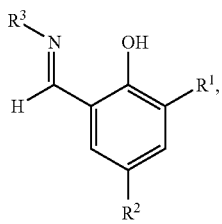

wherein $R^1$ is hydrogen, alkyl, cycloalkyl, aryl or aralkyl;
$R^2$ is hydrogen, halogen, alkyl, cycloalkyl, aryl, O-alkyl or aralkyl; and
$R^3$ is alkyl, cycloalkyl, aryl or aralkyl; and
wherein the phenoxyimine compound and the cyclopentadienyl, indenyl, or fluorenyl derivative are bridged via an alkynyl group.

8. A catalyst complex according to claim 7, wherein the metals are chosen from the group consisting of Ti, Hf and Zr.

9. A multinuclear catalyst complex according to claim 7, wherein the multinuclear catalyst complex is a trinuclear catalyst complex.

10. A process for preparing a multinuclear catalyst complex according to claim 7, comprising the steps of bonding a substituted phenoxyimine compound to a substituted cyclopentadienyl, indenyl or fluorenyl derivative to obtain a ligand framework and reacting at least one ligand framework with an active metal.

11. A process according to claim 10, wherein the phenoxyimine compound and the cyclopentadienyl, indenyl or fluorenyl derivative are bonded by a Sonogashira reaction.

12. A process according to claim 11, wherein the metal is selected from the group consisting of Ti, HF and Zr.

13. A process according to claim 10, wherein the metal is selected from the group consisting of Ti, HF and Zr.

14. A catalyst complex according to claim 1, wherein the catalyst complex is a trinuclear complex.

15. A catalyst complex according to claim 5, wherein the catalyst complex is a trinuclear complex.

* * * * *